US009381213B2

(12) United States Patent
Szilbereky et al.

(10) Patent No.: US 9,381,213 B2
(45) Date of Patent: Jul. 5, 2016

(54) ANTIVIRAL AND IMMUNE STIMULANT PHARMACEUTICAL COMPOSITION

(75) Inventors: Jenö Szilbereky, Budapest (HU); Andrea Jednákovits, Szentendre (HU); Ernöné Koltai, Budapest (HU); Gyula Orbán, Szekszárd (HU); Katalin Bíró, Budapest (HU)

(73) Assignee: SINNEX MUSZAKI FEJLESZTO ES TANACSADO KFT, Budapest (HU)

( * ) Notice: Subject to any disclaimer, the term of this patent is extended or adjusted under 35 U.S.C. 154(b) by 2303 days.

(21) Appl. No.: 11/792,247

(22) PCT Filed: Nov. 15, 2005

(86) PCT No.: PCT/HU2005/000122
§ 371 (c)(1),
(2), (4) Date: Aug. 3, 2007

(87) PCT Pub. No.: WO2006/059169
PCT Pub. Date: Jun. 8, 2006

(65) Prior Publication Data
US 2008/0131519 A1  Jun. 5, 2008

(30) Foreign Application Priority Data
Dec. 3, 2004  (HU) ..................... 0402490

(51) Int. Cl.
A61K 33/04    (2006.01)
A61K 31/198   (2006.01)
A61K 31/23    (2006.01)
A61K 33/30    (2006.01)

(52) U.S. Cl.
CPC .............. A61K 33/04 (2013.01); A61K 31/198 (2013.01); A61K 31/23 (2013.01); A61K 33/30 (2013.01)

(58) Field of Classification Search
None
See application file for complete search history.

(56) References Cited

U.S. PATENT DOCUMENTS

| 5,776,978 A * | 7/1998 | Bruzzese |
| 6,284,268 B1 * | 9/2001 | Mishra et al. |
| 2003/0180387 A1 * | 9/2003 | Kossler et al. |
| 2003/0203973 A1 * | 10/2003 | Cooper et al. |

FOREIGN PATENT DOCUMENTS

| DE | 39 07 649 A1 | 9/1989 |
| DE | 39 07 688 A1 | 9/1989 |
| EP | 891771 A1 * | 1/1999 |
| GB | 2216421 A * | 10/1989 |
| HU | 199775 B | 10/1989 |
| HU | 209973 B | 1/1995 |
| JP | 02022228 A * | 1/1990 |

OTHER PUBLICATIONS

Loftsson, T et al. Pharm. Pharmcol. Commun. (1998); 4: 287-291. Fatty acid extract erom cod-liver oil: Activity against herpes simplex virus and enhancement of transdermal delivery of acyclovir In-vitro.*
Miller, CS et al. General Denistry (1984); 32(6): 490-493. Use of lysine in treating recurrent oral herpes simples infections.*
Arens, M et al. Journal of Clinical Microbiology (2000); 38(5): 1758-1762. Zinc salts inactivate clinical isolates of herpes simplex virus in vitro.*
Balch, JF et al.Prescription for Nutritional Healing: A Practical A-Z Reference to Drug-free Remedies Using Vitamins, Minerals, Herbs and Food Supplements. 1997 New York. Avery Publications. "Herpesvirus Infection", pp. 317-319.*
Hamazaki, "Intervenous Infusion of n-3 polyunsaturated fatty acids," Proc. of Sox. for Exp. Biol. & Med., vol. 200, No. 2, pp. 171-173 (1992). (Abstract Only).

* cited by examiner

Primary Examiner — Susan Hoffman
(74) Attorney, Agent, or Firm — Young & Thompson

(57) ABSTRACT

The invention relates to a novel antiviral and immune-simulating pharmaceutical composition, containing as active ingredient 20-85 mass % of a ω-3-polyunsaturated fatty acid ester, in fish oil concentrate containing 20-70 mass % of a 5,8,11,14,17-eicosapentaenic acid ester and a 4,7,10,13,16, 19-docosahexaenic acid ester, further 1-lysine of a salt thereof, optionally a zinc salt, selenium or a selenium compound, as well as additives and carrier ingredients.

17 Claims, No Drawings

ANTIVIRAL AND IMMUNE STIMULANT PHARMACEUTICAL COMPOSITION

The invention relates to antiviral and immune stimulant pharmaceutical composition.

It is known that ω-3-polyunsaturated fatty acids, among them 5,8,11,14,17-eicosapentaenic acid (hereinafter EPA) as well as 4,7,10,13,16,19-docosahexaenic acid (hereinafter DHA) exhibit antiviral effects. Initial in vitro experiments (see e.g. Antimicrobial Agents and Chemotherapy 12, 523 (1977)) have been confirmed both by in vivo animal experiments (see e.g. U.S. Pat. No. 4,513,008) and clinical data (see. e.g. J. of Immunology 134, 1914 (1985) or Clin. Exp. Immunol. 65, 473 (1986)).

Is has been also known that 1-lysine inhibits under in vitro conditions the replication of Herpes simplex virus (HSV) in human cells (see J. Vact. 87, 609 (1964)). Clinical investigations have established however, that 1-lysine exerts only marginal curative effect in HSV infections (see Dermatologica, 156, 257 (1978)).

In the literature it is generally accepted, that HSV replication along with other viral infections is associated with a compromised immune system. It is also known that both EPA and DHA and their derivatives take effect on the immune system by inhibiting the prostaglandin system. This means that these agents are capable to inhibit and/or correct immune deficiency, certain autoimmune processes and tumor genesis elicited by age and/or detrimental environmental effects (see J. of Immunology 134, 1914 (1985) or Immunology 46, 819 (1982) or Eur J. Clin. Nutr. 56 Suppl. 3, 14-19 (2002)).

An interesting discovery is disclosed in HU-Pat. 199,775, according to which the salts of C 18 to 24 fatty acids containing at least two double bonds with amino acids (preferably with 1-lysine, 1-tyrosine, 1-hystidine, 1-alanine or 1-ornithine) are suitable as active ingredients in antiviral compositions. This information was supported by in vitro experiments the efficacy of such compositions in inhibiting virus proliferation. The most significant results were reported by tyrosine salts of polyunsaturated fatty acids. A disadvantage of this invention is that the salt formation often resulted in paste like products, which were difficult to purify and characterize (see e.g. Examples 10-14 of the quoted patent specification). Even the more readily crystallizing salts had non-defined melting points. Accordingly, the products obtained in the way disclosed by the patent specification referred often showed varying coloration indicating impurity and uncertain qualities of the active ingredient.

Elimination of the disadvantages of the above mentioned method was attempted by the authors of the HU-Pat. 209,973. In this process instead of using the salts of the fatty acids with amino acids 1-lysine, 1-tyrosine or derivatives thereof were mixed with ω-3-polyunsaturated fatty acids or salt thereof in a molar ratio of 1:4-4:1. The mixture obtained in this way and serving as active ingredient, was transformed—using standard procedures of drug formulation—to a pharmaceutical composition. These compositions specified in the description exhibited an immune stimulating effect, however, as a drawback, even the two most effective compositions (l-tyrosine—fatty acid and 1-lysine monohydrate—fatty acid mixtures) needed to be stabilized by an antioxidant. In spite of the use of stabilizers, as shown by our own experiments, mixtures prepared following the specifications of the above patent, proved to be unsuitable as components for a pharmaceutical composition of sufficient stability.

There are data informing that HSV viruses isolated from clinical samples can be inactivated to a certain degree by in vitro treatment with a zinc salt. The degree of inactivation depends on the HSV strain, concentration of the zinc salt and the duration of the treatment (Max Arens and Sharon Travis: J. of Clinical Microbiology, 38, 1758-1762 (2000)).

Selenium, apart from playing a key role in the activation of the enzyme glutathione peroxidase and thereby in oxidative stress conditions, can, in the form of selenoproteins, act on virus replication. On introduction of selenium in vitro inhibition of HIV virus replication was demonstrated with chronically infected T-lymphocites (Hori et al.: AIDS Res. Human Retroviruses 13, 1325-32 (1997)). The objective of the present invention is the preparation of a pharmaceutical composition of enhanced efficacy, which is not only devoid of all the problems associated with large-scale technology, composition and stability inherent in prior procedures, but also offers valuable additional benefits.

The present invention is based on the recognition that the above objective can be realized if, instead of the free ω-3-polyunsaturated fatty acids—namely EPA and DHA—the esters thereof are used, further that the effect of these esters is enhanced in a synergistic way by the addition of 1-lysine or its salts, optionally by adding a zinc salt or selenium or selenium compound. Unexpectedly, combinations obtained in this manner, show—in comparison with known compositions—lower toxicity and enhanced efficacy, in other words the therapeutic indices of combinations produced on the basis of the invention disclosed above are more favorable than those of any known similar composition.

The invention thus relates to a antiviral and immune-stimulant pharmaceutical composition which contains, as active ingredient 20-85 mass % of a ω-3-polyunsaturated fatty acid ester, specifically 20-70 mass % of a fish oil concentrate containing esters of 5,8,11,14,17 eicozapentaenoic acid and 4,7,10,13,16,19·docozahexaenoic acid, 1-lysine or its salts, optionally a zinc salt, selenium or a selenium compound, as well as additive and carrier.

The product, according to the present invention, contains in one of its preferable embodiments a ω-3-polyunsaturated fatty acid in form of their esters formed with primary, secondary or tertiary alcohols, preferably the ethyl or glycerol esters, as well as the 1-lysine salt 1-lysine hydrochloride.

The amount of the ω-3-polyunsaturated fatty acid ester containing fish oil concentrate is preferably 30 to 70 mass %, more preferably 40 to 60 mass %, most preferably 55 to 60 mass %, wherein specifically 20 to 70 mass %, preferably 25 to 45 mass %, more preferably 30 to 40 mass %, most preferably 31 to 35 mass % 5,8,11,14,17-eicozapentaenic acid and 20 to 70 mass %, preferably 25 to 45 mass %, more preferably 30 to 40 mass %, most preferably 31 to 35 mass % 4,7,10,13,16,19-docozahexaenic acid is provided.

As a lysine salt, not only lysine hydrochloride, but also all pharmaceutically acceptable lysine salts cant be mentioned. Non limiting examples are lysine fumarate, maleate and oxalate. The amount of the lysine salt can range from one fourth of the equimolar amount of the ω-3-polyunsaturated fatty acid ester to four times amount thereof.

The concentration of the zinc salt is 1 to 10 mass %, preferably 2 to 6 mass %.

In another embodiment of the present invention, the composition contains as zinc salt zinc gluconate or zinc lactate, as selenium compound one or more natural selenium compounds incorporated into natural yeast.

The ω-3-polyunsaturated fatty acid esters applied as components of the composition specified in the present invention can mainly found in oils obtained from fish of the North Sea. From such fish oils by known procedures (see. e.g. J. Am. Chem. Soc, 59, 117 (1982)) fish oil concentrates containing 50-65 mass % of ω-3-polyunsaturated fatty acid esters 20-70% of which are esters of 5,8,11,14,17-eicozapentaenic acid and 4,7,10,13,16,19-docozahexaenic acid can be prepared.

The other essential component of the composition described in the present invention is 1-lysine1 or some 1-lysine salt, preferably with acetic or hydrochloric acid (see e.g. US Pharmacopoeia 27-NF 22 Supplement 2.)

The third component of the composition is a zinc salt, preferably zinc gluconate or zinc lactate (see. e.g. US Pharmacopoeia 27-NF 22 Supplement 2).

A further, but optional component of the composition described in the present invention is a selenium compound, which can be a selenium compound incorporated into natural yeast or any other selenium compound. The concentration of the selenium is 0.05 to 0.30 mass %, preferably 0.1 to 0.2 mass %, but not more than 75 μg.

The above specified active ingredients can be formulated using methods generally known in the formulation of pharmaceutical compositions to obtain a composition formulated known per se preferably as enclosed into a soft gelatin capsule. As additives and/or auxiliary materials, preferably silica gel, glycerol, dyes and other substances can be used.

Antiviral and immune stimulating effect of the composition described in the present invention is verified as follows:

A. Description of Test Substances and Test Methods

I. Codes for and Composition of Test Substances

SIN-E1: Salt of ω-3-polyunsaturated fatty acids with 1-lysine monohydrate (see: Example 1 of Hungarian patent 209,973).

SIN-E2: ω-3-polyunsaturated fatty acid ester+1-lysine-.HCl (see: Example 3 of the present application).

SIN-E3: ω-3-polyunsaturated fatty acid ester+1-lysine-.HCl+calcium gluconate (see: Example 1 of the present application).

II. Test Methods

1. Toxicity Test on Primary Monkey Kidney Cell Culture

Primary monkey kidney cell were treated with various dilutions (1:3, 1:10, 1:30, 1:100) of the test substances SIN-E1, SIN-E2 and SIN-E3. After incubation for 3 hours eventual toxic effects of the substances on the tissue was investigated (see Arens, M. and Travis, S.: J. of Clinical Microbiology, 38, 1758-1762 (2000)).

2. Study of the Antiviral Effects of the Test Substances

Study of the infection of secondary monkey kidney cell cultures with viruses pretreated with the test substances SIN-E1, SIN-E2 and SIN-E3.

Viruses of various dilutions were incubated for 1 hours with various dilutions of the test substances in a way that they were mixed in a 1:1 ratio, corresponding to a dilution of 0.5% (see Table 1), followed by infecting of a secondary monkey kidney cell culture with the pretreated virus. On the seventh day the cytopathogenic effect of Herpes simplex virus (HSV) on monkey kidney cells was determined by microscopic examination for both untreated viruses and those pretreated with test substances SIN-E1, SIN-E2 and SIN-E3. The purpose of this test was to determine the direct antiviral effect of the test substances on the cells (see Lawetz, C., Liuzzi, M.: Antiviral Res. 39 (1), 35-46 (1998)).

3. Study of the Effect of Serum Proteins on the Virus Inactivating Effect of Test Substances SIN-E1, SIN-E2 and SIN-E3.

With dilutions showing total inactivation in experiments described under point 2 as well as with the next higher dilution the experiments were repeated with a maintenance culture medium containing 10% of veal serum and with a blank without serum and on the seventh day the experiment was evaluated as under point 2.

4. Evaluation

Cells were inspected with an inverse microscope, in case of toxicity studies after 3 hours of incubation, and after 7 days in case of the study of antiviral effect. Changes in morphology, development of cavities, separation, as well as damage of cell walls were recorded.

B. Efficacy Studies

1. Study of the Toxicity of the Test Substances in Tissue Culture

Tissue: secondary monkey kidney cell culture, cell number is $5 \times 10^6$.

continuous dilutions of scale 2 were prepared from all three test substances, applied to the tissue, followed by incubation at 37 C.° for 3 hours, the blank only contained the tissue, after 3 hours the material was drawn off, 100 μl of Parker's culture medium containing 2% of veal serum was added to the whole plate and morphological changes were registered by microscopy, based on examination after 3 hours substances SIN-E1 proved to be non-toxic in a dilution of 1:32768, while substances SIN-E2 and SIN-E3 were non-toxic in a dilution of 1:2048, next day the examination by microscopy was repeated and the same results were obtained, in the following with SIN-E1 dilution 1:32768 was labeled as "Concentrated" while with SIN-E2 and SIN-E3 it was dilution 1:2048. (Result recorded are shown in Table 1.)

TABLE 1

Comparison of the toxicity of substances SIN-E1, SIN-E2 and SIN-E3

| | 1:128 | 1:256 | 1:512 | 1:1024 | 1:2048 | 1:4096 | 1:8192 | 1:16384 | 1:32768 | 1:65536 | 1:131072 | 1:262144 |
|---|---|---|---|---|---|---|---|---|---|---|---|---|
| SIN1 | | | | | | + | + | + | − | − | − | − |
| SIN1 | | | | | | + | + | + | − | − | − | − |
| SIN1 | | | | | | + | + | + | − | − | − | − |
| SIN2 | + | + | + | + | − | − | − | − | − | − | − | − |
| SIN2 | + | + | + | + | − | − | − | − | − | − | − | − |
| SIN2 | + | + | + | + | − | − | − | − | − | − | − | − |
| SIN3 | + | + | + | + | − | − | − | − | − | − | − | − |
| SIN3 | + | + | + | + | − | − | − | − | − | − | − | − |
| SIN3 | + | + | + | + | − | − | − | − | − | − | − | − |
| negative control | − | − | − | − | − | − | − | − | − | − | − | − |
| negative control | − | − | − | − | − | − | − | − | − | − | − | − |

Symbols used in Table 1:
+ = cytotoxic dose
− = dose not yet cytotoxic

Evaluation of the Tests:

Toxicity studies performed clearly show that substance SIN-E1 was more toxic by at least one order of magnitude than substances SIN-E2 and SIN-E3. It is obvious that toxicity disappears with test substances SIN-1 at a final dilution of 1:32768 of the standard solution, while with substances SIN-E2 and SIN-E3 it disappears at a final dilution of already 1:2048. In course of the following studies the above final dilutions were taken as basis.

2. Examination of the Antiviral Effect of Test Substances

Tissue: secondary monkey kidney cell culture, cell number: $5 \times 10^6$.

Dilutions of $10^{-1}$-$10^{-8}$ were prepared from the virus and its infective titer was determined. In the Table 2 the negative logarithms/0.1 ml of the infective titer were entered.

Dilutions of 1:32768 were prepared from test substance SIN-E1, while dilutions of 1:2048 were prepared from test substances SIN-E2 and SIN-E3, respectively. These dilutions were labeled as "concentrated".

Tests were carried out with dilutions of 1:3, 1:10, 1:30 and 1:100 of the "concentrated" dilutions.

Dilutions of the virus and the test substance were mixed in a 1:1 ratio.

This was followed by incubation for 1 hour.

Thereafter the culture medium over the tissue was drawn off and 100 μl portions were applied onto the appropriate rows from the mixture of virus and test substance dilutions.

Incubation for 1 h at 37° C. followed.

The substance was drawn off and 100 μl of Parker's culture medium containing 2% of calf serum was added to it.

The sample was kept at 37° C. and evaluated by microscopy over 7 days and compared with the untreated virus.

Results are shown in Table 2.

TABLE 2

Testing for antiviral activity

| | Dilution of test ubstances, mg/mL | | | | |
|---|---|---|---|---|---|
| | 1:3 1.5 | 1:10 0.5 | 1:30 0.15 | 1:100 0.05 | Virus control |
| SIN-E1 | 0* | 0* $p < 0.01$ | 4.0 | 5.15 | 5.15 |
| SIN-E2 | 0* | 0* $p < 0.01$ | 3.2 | 4.8 | 5.15 |
| SIN-E3 | 0* | 0* $p < 0.01$ | 0* $p < 0.01$ vscontrol $p < 0.05$ vs SIN-E2 | 3.5 | 5.15 |

Symbols in Table 2:
0* = total inhibition

Evaluation of the Results

The studies performed have demonstrated that all three test substances completely inhibited virus proliferation in dilutions 1:3 (1.5 mg/mL) and 1:10 (0.5 mg/mL). Partial inactivation within 1 hour could be observed even at dilutions of 1:30 (0.15 mg/mL) for substances SIN-E1 and SIN-E2, while for SIN-E3 complete inhibition was observed even at this dilution, which was significant in comparison both to SIN-E2 and the control. With SIN-E3 partial inactivation was found at a dilution of 1:100 (0.05 mg/mL), but this result is statistically insignificant.

3. Study of the Effect of Serum Proteins on the Virus Inactivating Effect of SIN-E1, SIN-E2, and SINE-3

Experiments were performed as described under point 2.

TABLE 3

Antiviral activity of test substances in the presence of calf serum

| | Dilution of test substances, mg/mL | | | | |
|---|---|---|---|---|---|
| | 1:3 1.5 | 1:10 0.5 | 1:30 0.15 | 1:100 0.05 | Virus control |
| SIN-E1 | 0* | 0* $p < 0.01$ | 4.0 | 5.15 | 5.15 |
| SIN-E2 | 0* | 0* $p < 0.01$ | 3.2 | 4.8 | 5.15 |
| SIN-E3 | 0* | 0* $p < 0.01$ | 0* $p < 0.01$ vscontrol $p < 0.05$ vs SIN-E2 | 3.5 | 5.15 |

Symbols in Table 3:
0* = total inhibition

TABLE 4

Antiviral activity of the test substances in a medium devoid of calf serum

| | Dilution of test substances, mg/mL | | | | |
|---|---|---|---|---|---|
| | 1:3 1.5 | 1:10 0.5 | 1:30 0.15 | 1:100 0.05 | Virus control |
| SIN-E1 | 0* | 0* $p < 0.01$ | 4.2 | 5.15 | 5.15 |
| SIN-E2 | 0* | 0* $p < 0.01$ | 3.5 | 4.9 | 5.15 |
| SIN-E3 | 0* | 0* $p < 0.01$ | 0* $p < 0.01$ vscontrol $p < 0.05$ vs SIN-E2 | 3.7 | 5.15 |

Symbols in Table 4:
0* = total inhibition

Evaluation of the Tests

The inactivating activity of test compounds towards herpes virus is not influenced by the presence of a protein, because it manifested itself both in a serum free medium (see Table 4) and in a medium containing 10% of fetal calf serum (see Table 3).

In summary, it can be stated that according to the study of the influence of serum proteins, the compositions covered by the present patent exhibited significant additional activity as compared to prior data in the literature (see e.g. U.S. Pat. No. 4,513,008, inventors, E. Recivi et al.), claiming that the infectivity of viruses with capsids was impaired or completely eliminated by various unsaturated fatty acid compositions owing to disintegration of surface structures of the virus. According to other literature data (see e.g. Vollenbroich, D. et al.: Biologicals. Sept.; 25 (3): 289-97 (1997)) the virus inactivating activity of unsaturated fatty acids applied was cancelled by a minimal amount of serum proteins, and were therefore useless in therapy. In contrast in our own experiments in primary monkey kidney tissues the herpes virus inactivating effect of our compositions was not inhibited even by presence of 10% of fetal calf serum.

Advantages of the pharmaceutical compositions claimed by the present application can be summarized as follows:

in contrast to the prior art, the present invention permits the preparation of a stable pharmaceutical composition of long shelf life having the advantage that oxidation of ω-3-polyunsaturated fatty acidson standing is effectively prevented, application of the method specified in the present invention supplies a simple and economic preparation of additional combinations containing other and/or new antiviral agents, toxicity of the esters of ω-3-polyunsaturated fatty acids, as well as of compositions containing them were proven to be lower than that of the parent ω-3-polyunsaturated fatty acids or compositions containing thereof, with combinations prepared according to the present invention enable a biologically more versatile and more flexible antiviral treatment, which provides, at the same time more efficient inhibition of virus replication, further, the procedure described in the present invention eliminates the technological problems associated with the preparation of salts of ω-3-polyunsaturated fatty acids with basic components and costs incurred by the mentioned difficulties.

Compositions made according to the present invention are illustrated by the following examples:

EXAMPLE 1

Preparation in a Capsulated Form (Coded SIN-E3 in the Tables)

A mixture of esters of ω-3-polyunsaturated fatty acids originating from enriched marine fish oil (362 g), containing 35 mass % of 5,8,11,14,17-eicosapentaenic acid ethyl ester (EPA ethyl ester), and 25 mass % of 4,7,10,13,16,19-docosahexaenic acid ethyl ester (DHA ethyl ester), is mixed at room temperature with 1-lysine hydrochloride (203 g) and zinc gluconate (30 g). In this way a homogenous mixture is obtained, which is then supplemented with colloidal silica gel (25 g) and lecithin (1 g). After further homogenization the substance is filled, using process known per se, into 1000 soft gelatin capsules.

EXAMPLE 2

Preparation in a Capsulated Form

In every respect the procedure described in Example 1 is followed with the difference that the composition contains a mixture of ω-3-polyunsaturated fatty acid ethyl esters (362 g) composed of 32.8 mass % of 5,8,11,14,17-ecosapentaenic acid ethyl (EPA ethyl ester), and 22.2 mass % of 4,7,10,13,16,19-docosahexaenic acid ethyl ester (DHA ethyl ester), and the active ingredients and additives specified in Example 1 but is also supplemented with selenium incorporated into natural yeast (1 g).

EXAMPLE 3

Preparation in a Capsulated Form (Coded SIN-E2 in the Tables)

A mixture of esters of ω-3-polyunsaturated fatty acids originating from enriched marine fish oil (362 g), containing 35 mass % of 5,8,11,14,17-eicosapentaenic acid ethyl (EPA ethyl ester), and 25 mass % of 4,7,10,13,16,19-docosahexaenic acid ethyl ester (DHA ethyl ester) is mixed at room temperature with 1-lysine hydrochloride (203 g). In this way a homogenous mixture is obtained, which is then supplemented with colloidal silica gel (25 g) and lecithin (1 g). After further homogenization the substance is filled—using process known per se—into 1000 soft gelatin capsules.

EXAMPLE 4

Preparation in a Capsulated Form

The process described in Example 1 is followed in every respect, except that instead of a mixture of ω-3-polyunsaturated fatty acid ethyl esters, a mixture of triglyceride ester of 5,8,11,14,17-eicosapentaenic acid (EPA triglyceride ester) and a triglyceride ester of 4,7,10,13,16,19-docosahexaenic acid (DHA triglyceride ester) are used.

What we claim is:

1. An antiviral and immune stimulating pharmaceutical composition, comprising:
   as active ingredients:
   (i) 20-85 mass % of ω-3-polyunsaturated fatty acid esters, in marine fish oil concentrate containing 20-70 mass % of a 5,8,11,14,17-eicosapentaenic acid ester and a 4,7,10,13,16,19-docosahexaenic acid ester, and
   (ii) 1-lysine, or a salt thereof, in an amount ¼ to 4 times of the mass % of said ω3-polyunsaturated fatty acid esters;
   optionally ingredients selected from the group consisting of 1 to 10 mass % zinc salt, 0.05 to 0.30 mass % selenium containing yeast, wherein said selenium containing yeast contains no more than 75 μg selenium or a selenium compound, additive ingredients, carrier ingredients, and combinations thereof.

2. The pharmaceutical composition according to claim 1, wherein the composition comprises 30 to 70 mass % ω-3-polyunsaturated fatty acid ester containing fish oil concentrate, and
   wherein 20 to 70 mass % 5,8,11,14,17-eicozapentaenic acid and 20 to 70 mass % 4,7,10,13,16,19-docozahexaenic acid is present in the marine fish oil concentrate.

3. The pharmaceutical composition according to claim 2 comprising:
   a ω-3-polyunsaturated fatty acid esterified with a primary, secondary or tertiary alcohol, and
   an 1-lysine salt selected from the group consisting of 1-lysine hydrochloride, 1-lysine fumarate, 1-lysine maleate and 1-lysine oxalate.

4. The pharmaceutical composition according to claim 2 comprising 1 to 10 mass % zinc salt, wherein the zinc salt is zinc gluconate or zinc lactate.

5. The pharmaceutical composition according to claim 2 comprising 0.05 to 0.30 mass % selenium containing yeast, wherein said selenium containing yeast is a selenium compound or selenium compounds incorporated into natural yeast.

6. The pharmaceutical composition according to claim 1 comprising:
   a ω-3-polyunsaturated fatty acid esterified with a primary, secondary or tertiary alcohol; and
   an 1-lysine salt from the group consisting of 1-lysine hydrochloride, 1-lysine fumarate, 1-lysine maleate and 1-lysine oxalate.

7. The pharmaceutical composition according to claim 6 comprising 1 to 10 mass % zinc salt, wherein the zinc salt is zinc gluconate or zinc lactate.

8. The pharmaceutical composition according to claim 6 comprising 0.05 to 0.30 mass % selenium present as selenium containing yeast, wherein said selenium containing yeast is a selenium compound or selenium compounds incorporated into natural yeast.

9. The pharmaceutical composition according to claim 1 comprising 1 to 10 mass % zinc salt, wherein the zinc salt is zinc gluconate or zinc lactate.

10. The pharmaceutical composition according to claim 9 comprising 0.05 to 0.30 mass % selenium present as selenium containing yeast, wherein said selenium containing yeast is a selenium compound or selenium compounds incorporated into natural yeast.

11. The pharmaceutical composition according to claim 1 comprising 0.05 to 0.30 mass % selenium containing yeast, wherein said selenium containing yeast is a selenium compound or selenium compounds incorporated into natural yeast.

12. A method of preparing a pharmaceutical composition for the treatment of viral infections, comprising:
   mixing at room temperature 20-85 mass % of ω-3-polyunsaturated fatty acid esters, in marine fish oil concentrate containing 20-70 mass % of a 5,8,11,14,17-eicosapentaenoic acid ester and a 4,7,10,13,16,19-docosahexaenoic acid ester with 1-lysine or a salt thereof, optionally ingredients selected from the group consisting of 1 to 10 mass % zinc salt and 0.05 to 0.30 mass % selenium containing yeast, wherein said selenium containing yeast containing no more than 75 μg selenium or a selenium compound, combination thereof.

13. A method of treating viral infections comprising:
   administering to a subject in need there of an effective amount of the pharmaceutical composition according to claim 1.

14. A method of treating viral infections comprising:
   administering to a subject in need there of an effective amount of the pharmaceutical composition according to claim 2.

15. A method of treating viral infections comprising:
   administering to a subject in need there of an effective amount of the pharmaceutical composition according to claim 6.

16. A method of treating viral infections comprising:
   administering to a subject in need there of an effective amount of the pharmaceutical composition according to claim 9.

17. A method of treating viral infections comprising:
   administering to a subject in need there of an effective amount of the pharmaceutical composition according to claim 11.

* * * * *